(12) United States Patent
Ariessohn

(10) Patent No.: US 7,704,294 B2
(45) Date of Patent: Apr. 27, 2010

(54) AERODYNAMIC LENS PARTICLE SEPARATOR

(75) Inventor: Peter Ariessohn, Lake Tapps, WA (US)

(73) Assignee: Enertechnix, Inc., Maple Valley, WA (US)

( * ) Notice: Subject to any disclaimer, the term of this patent is extended or adjusted under 35 U.S.C. 154(b) by 721 days.

(21) Appl. No.: 11/597,075

(22) PCT Filed: May 24, 2005

(86) PCT No.: PCT/US2005/018325

§ 371 (c)(1),
(2), (4) Date: Nov. 20, 2006

(87) PCT Pub. No.: WO2005/117060

PCT Pub. Date: Dec. 8, 2005

(65) Prior Publication Data

US 2008/0022853 A1    Jan. 31, 2008

Related U.S. Application Data

(60) Provisional application No. 60/574,287, filed on May 25, 2004.

(51) Int. Cl.
*B01D 45/00* (2006.01)

(52) U.S. Cl. .................................. 55/434; 209/143
(58) Field of Classification Search ............... 55/434; 209/143
See application file for complete search history.

(56) References Cited

U.S. PATENT DOCUMENTS 6,698,592 B2 *   3/2004   Kenning et al. ............. 209/143

\* cited by examiner

*Primary Examiner*—Robert A Hopkins
(74) *Attorney, Agent, or Firm*—J. Michael Neary

(57) ABSTRACT

Respirable particles with diameters on the order of 0.05 to 10 microns entrained in an air stream, are concentrated in an aerodynamic lens (FIG. 2) for separation from the air steam. The entire structure is made by microfabrication techniques, such as silicon micro-machining which enables arrays of precisely aligned slit lenses to be made on a silicon chip. At a Reynolds number of 800, a slit 25 microns wide by 1 mm tall will pass a flow of only 0.28 liters per minute, but arrays of lenses (FIG. 4), stacked in parallel banks, multiplies the available flow rate. Placing a skimmer (27) at the exit of each silicon micro-machined lens in the assembly and connecting the skimmer channels in chimneys (55), allows the bulk of the gas flow to be stripped off while allowing the concentrated particle stream to pass into a region of much lower flow rate, thereby producing a highly concentrated aerosol in the low velocity stream.

12 Claims, 6 Drawing Sheets

AERODYNAMIC LENS PARTICLE SEPARATOR

This is related to U.S. Provisional Application No. 60/574,287 filed on May 25, 2004 entitled "Aerodynamic Lens Particle Concentrator" and to PCT Application No. PCT/US2005/018325 filed on May 24, 2005, which was published as International Publication No. WO 2005/018325 on Dec. 8, 2005, and entitled "Aerodynamic Lens Particle Separator".

This invention pertains to concentration of particles suspended in a gas stream, and more particularly to an aerodynamic lens device for separation of suspended particles from a gas stream to collect the particles for testing or the like, or for producing a gas stream that is substantially free of suspended particles in a particular size range.

BACKGROUND OF THE INVENTION

Atmospheric aerosols from natural, anthropogenic and industrial sources have long been recognized as a potential threat to human health. To that list of sources, chemical or biological warfare (CBW) agents due to acts of terrorism must now be added as a source of potentially lethal contamination. Effective sampling and concentration of CBW agents is a critical first step in the detection of these aerosols, and much effort has gone into developing effective methods for rapid screening and detection of CBW agents in samples which can then be analyzed to assess the risk of exposure to these aerosols. One major challenge that must be addressed by all aerosol samplers is that most aerosols occur at extremely low concentrations, or may be only a small fraction of the urban background aerosol distribution. Therefore, not only is it necessary to sample large volumes of air in order to collect sufficient material for accurate detection, but for most measurement techniques it is also necessary to concentrate the aerosol and restrict the fraction collected to a range of particle sizes that is of greatest importance for the target agents. This latter step can help focus collection efforts on particles that present the greatest hazard in terms of inhalation or lung deposition (i.e. respirable particles in the range <10 µm diameter), and also helps discriminate nuisance aerosols from the sampling train.

One widely accepted method currently used to concentrate ambient aerosol particles is to collect them on filter media. In this approach, a filter is loaded into a collection device and sampling occurs over a period of time to allow for collection of a sufficient mass of material to permit accurate measurement. With some devices, the filter media must be removed from the sampling device and delivered to a laboratory setting where gravimetric, microscopic, and chemical analyses can be performed. Each of these manual handling steps introduces some potential for sample contamination and loss of material; the entire process is very time consuming which precludes collection of real-time, continuous data and makes it difficult to develop highly resolved temporal profiles of aerosol variability. In other devices the measurement process is automated, but the information provided is quite limited. For instance, in the case of aethalometers a continuous tape of filter media is periodically exposed to sampled aerosol and the optical reflectance of the resulting spots is measured automatically.

One common device which is used to provide continuous concentration and size classification of aerosols is the virtual impactor. This device is capable of handling large volumes of ambient air and can achieve, at best, roughly a 30:1 concentration factor in each stage. However, these devices concentrate the large size class of particles and exhaust a dilute stream containing the finer fraction. Multiple stages can achieve greater concentration factors and concentrate particles in the respirable range, but internal losses and device complexity limit this technique above concentration factors of a few hundred.

Cyclones can be staged to achieve relatively high concentration factors, but commercial systems using this approach typically will either be small in size and have correspondingly low flow rates, or be large so as to achieve a high flow capacity but sacrifice concentration efficiency and sizing characteristics. Some commercial systems such as those offered by Innovatek use a parallel design of small cyclones to achieve high throughput and sizing characteristics, but the resulting device can be bulky, complex, costly to manufacture, and not well suited to personal monitoring applications or lightweight portable field instruments. Therefore a critical unmet need that remains is to develop a lightweight and inexpensive high-efficiency aerosol concentrator with the desired aerodynamic sizing characteristics.

In the past few years, several groups at Yale University, UC Riverside, U. of MN and two universities in South Korea have begun studying a completely new approach to particle concentration using aerodynamic lenses. Aerodynamic lenses consist of a series of orifices of decreasing size through which a dilute aerosol is aspirated. So long as the flow is laminar, particles smaller than a specific size and Stokes number are concentrated by fluid flow forces into a narrow beam along the centerline as the gas flows through the series of orifices, while the majority of the gas flow away from the centerline is left virtually free of particles. Thus, as shown in FIG. 1, particle trajectories may be concentrated in a cylindrical geometry aerodynamic lens, producing an aerosol beam with a diameter on the order of a millimeter or less.

Work on aerosol beam technology dates back at least as far as the 1970's, but this early work was limited to beams formed by expanding an aerosol into a vacuum chamber or accelerating an aerosol through a converging nozzle. Beginning in the 1990's a number of researchers began looking at forming aerosol beams with cylindrical aerodynamic lenses consisting of a series of progressively smaller orifices. This work is reported in papers by Prof. Fernandez de la Mora and his group at Yale University, and by Prof. Ziemann at U.C. Riverside, along with Profs. McMurry and Kittelson at U. of MN. In the late 1990's, J. Schreiner et. al. at the Max Planck Institute published two papers on focusing of aerosol particles at very low pressure using aerodynamic lenses, and in 2003, two groups in Korea published papers on cylindrical and slit lens concentrators operating at atmospheric pressure.

Aerodynamic lenses utilizing circular orifices have been shown to be capable of achieving aerosol beam concentration factors of $10^4$ to $10^6$. Initially these aerodynamic lenses were designed for stratospheric research at extremely low pressures, but more recent work has shown that they can be operated successfully at somewhat higher pressures. It has been shown that tightly focused aerosol beams can be formed even at atmospheric pressure, and simulation has shown that a slit lens configuration operating at atmospheric pressure can achieve concentration factors of at least 100 for polydisperse aerosols containing particles as small as 0.3 microns. The slit lens arrangement focuses the particles into a sheet rather than a cylindrical beam.

Aerosol sampling devices constitute a core component of most aerosol monitoring systems. The three major market segments for such devices are air monitoring, chemical and biological agent detection, and on-site industrial process monitoring. The market for air monitoring equipment in 2002 totaled $1.07 billion and is estimated to grow to $1.7 B by 2007. The world market in 2002 is estimated to be $3.0 B. The market for chemical and biological agent detectors was estimated to be $265 M in 2000 and scheduled to grow to $494 M. by 2007. The market for industrial and laboratory particle analysis equipment is estimated to be 20% as large as the market for air monitoring equipment. Accordingly, there has been a large and growing need for economical effective, real-time aerosol concentrators that can be assembled in modules to meet the flow rate and particle size requirements of a particular application. An aerosol concentrator, based on aerodynamic lens technology that is capable of achieving very high concentration factors in a very compact device and can be fabricated using low cost processes would be a very desirable contribution to technology. Fabricating such a device using micro-machining techniques in silicon, one of a variety of stereo micro-lithography or other rapid prototyping techniques, or more exotic methods such as X-ray or UV LIGA would offer many significant advantages, including low cost, compact size, high reliability, the potential to produce a highly parallel physical architecture that allows many individual aerodynamic lenses, each having very low throughput, to be combined to achieve high overall throughput, extremely high precision and repeatability in the manufacturing process which assures optimal and repeatable performance from one device to the next, and the potential to couple this device with MEMS sensors and integrated electronics.

SUMMARY OF THE INVENTION

This invention provides an aerodynamic lens capable of concentrating respirable particles with diameters ranging from 0.3 to 10 microns. It utilizes a parallel array of aerodynamic lenses, each having an input end and an output end, and an internal flow channel extending between the input and output ends, with a series of internal focusing slit orifices of decreasing width from input to output end through baffles extending laterally into the internal flow channel, and a final slit orifice through which a concentrated aerosol sheet emerges from the output end.

The dimension of the final focusing orifice or slit is preferably on the order of 25 to 50 microns for optimal removal of the target particle size range. The small size of this orifice or slit creates two practical problems. First, accurately machining components with such small dimensions by traditional methods can be accomplished only by using specialized techniques such as laser cutting or drilling or electric discharge machining (EDM), and precisely aligning a series of such small openings is a major challenge if they are fabricated as separate components and then combined into a single assembly. Second, the maximum flow rate that can be accommodated by such small openings is extremely small. The use of a slit lens instead of a circular orifice provides some improvement in flow rate due to the substantially greater cross sectional area of the opening, but the flow rates for such a device are still extremely small. At a Reynolds number of 800, a slit 25 microns wide by 1 mm tall will pass a flow of only 0.28 liters per minute. However, constructing arrays of aerodynamic lenses using micro-fabrication techniques will allow particle concentrators of any desired flow volume capacity to be economically built to provide a capability to science and industry that does not exist using currently available technologies.

Placing a skimmer at the exit of each micro-fabricated lens in the assembly allows the bulk of the gas flow to be stripped off while allowing the concentrated particle stream to pass into a region of much lower flow rate, thereby producing a highly concentrated aerosol in the low velocity stream.

DESCRIPTION OF THE DRAWINGS

The invention and its many attendant features and benefits will become better understood upon reading the following description of a preferred embodiment in conjunction with the following drawings, wherein.

DESCRIPTION OF THE PREFERRED EMBODIMENTS

Figure 1:
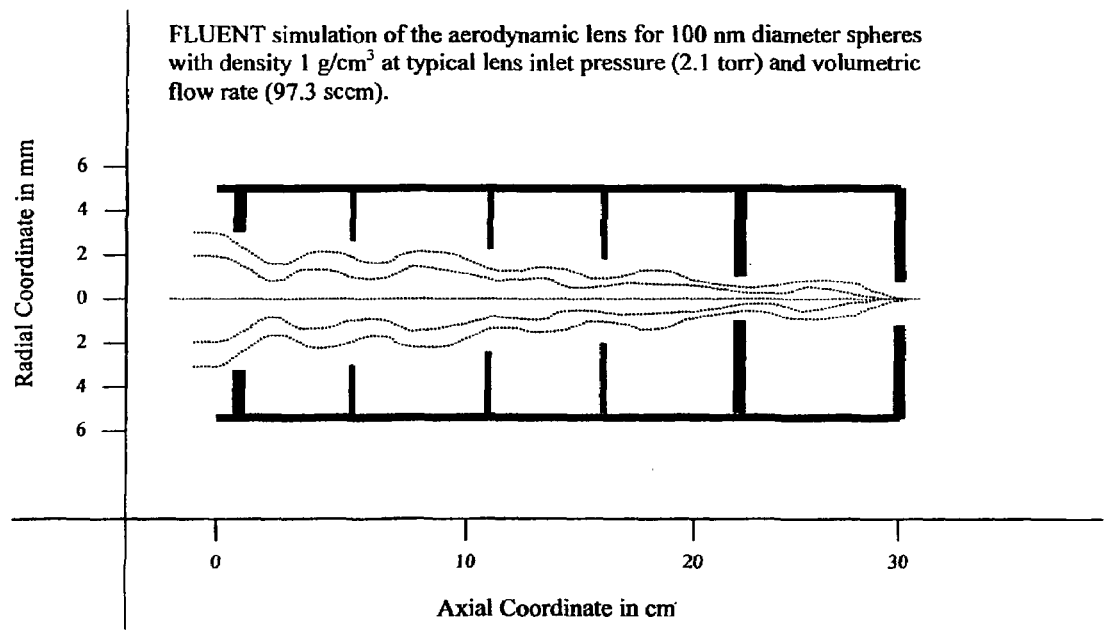
FIG. 1 is an illustration of particle trajectories in an aerodynamic lens simulation.
Figure 2:
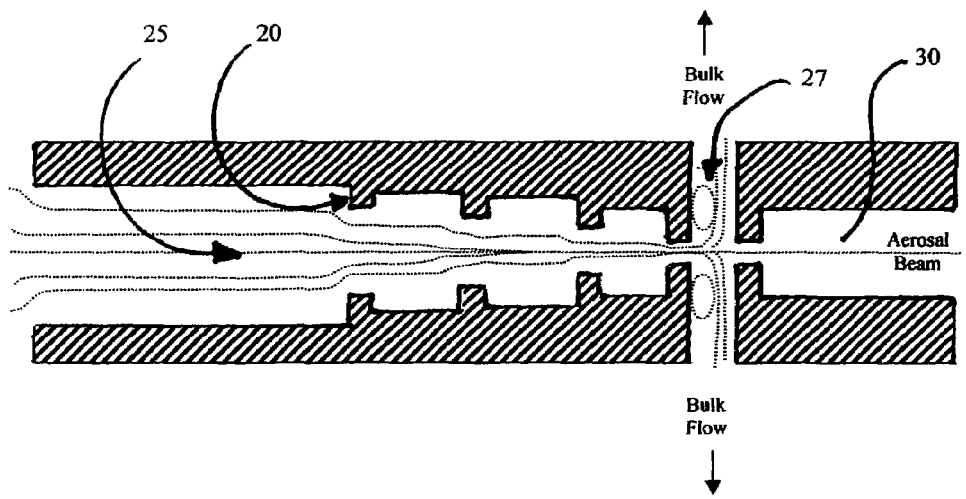
FIG. 2 is a sectional plan view of an aerodynamic lens with skimmer, in accordance with this invention.

Turning now to the drawings, wherein like reference characters designate identical or corresponding parts, and more particularly to FIG. 2 thereof, an aerodynamic aerosol particle separator is shown having a train of four slit lenses in series. Each lens includes a slit baffle 20 projecting laterally into a longitudinal channel 25. The channel 25 becomes progressively narrower at each lens and the slit in each baffle also becomes narrower for each successive lens. A skimmer 27 just upstream of a collection chamber 30 allows for exit of clean air from the particle-entraining air flow, as shown. The light lines depict fluid streamlines and the darker stream lines depict particle trajectories.

Figure 3:
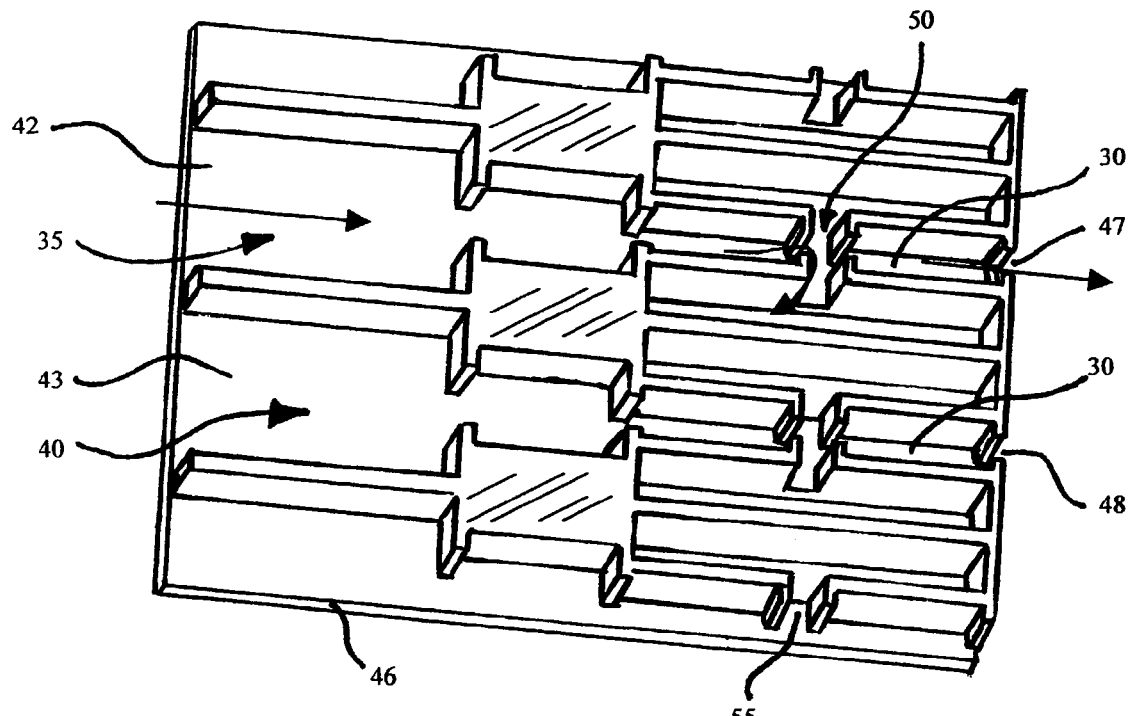
FIG. 3 is a layout for an array of silicon aerodynamic lens aerosol concentrators bonded to a support layer.

In FIG. 3, a micro-fabricated array of two parallel aerosol particle separator slit lens trains 35 and 40 is shown having channels 42 and 43 extending through a fabricated structure 45. An aerosol flows through the channels 42 and 43 in the direction indicated by the arrows. Aerosol particles concentrated in the lens array flow from the collection chambers 30 out of the lens array through exit slits 47 and 48, and particle-free air flows out of the channels through exit skimmer openings 50 and vertical bulk flow chimneys 55. Micro-fabrication techniques, described in detail below, can be used to produce vertical structures in the required shapes, such as walls, baffles and slits, in a structure that is on the scale of about 1 mm thick. Thin sheets or films 46 cover both surfaces to contain the air flow within the channels, provide support, and maintain precise positioning of the structures. In FIG. 3, only the lower glass support 15 is shown. Openings are cut in the sheets 46 to match the chimneys 55, thereby providing gas flow passages perpendicular to the longitudinal axis of the channels 42, 43 to exhaust particle-free bulk flow from the skimmers 50. the micro-fabrication techniques are selected for the ability of making walls that are essentially vertical and of uniform thickness. These characteristics are desirable in this application.

Figure 4:
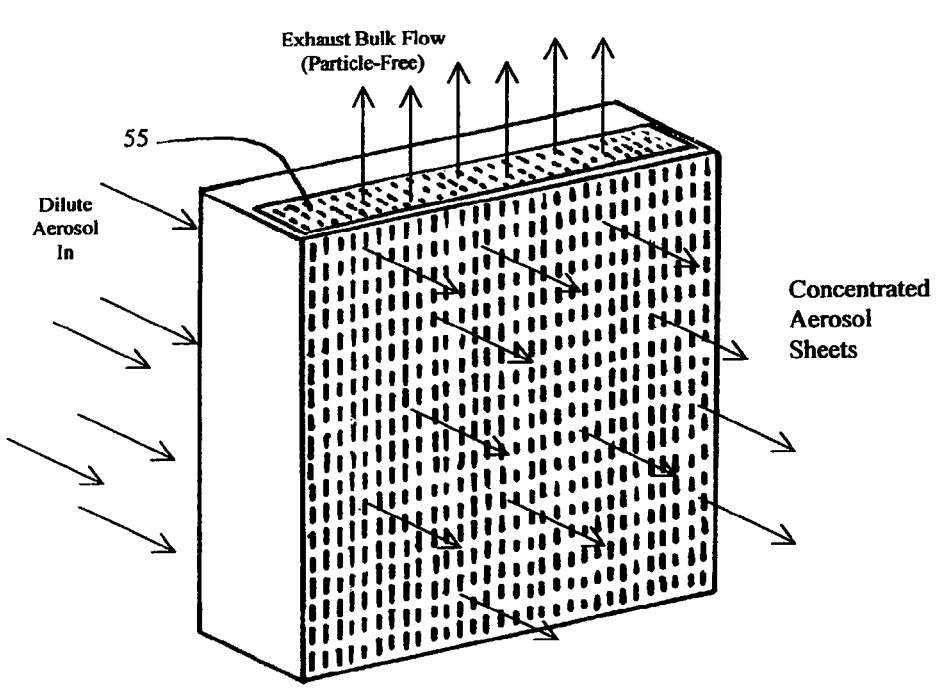
FIG. 4 is a perspective view of an assembled aerosol lens array stack.

Although only two aerosol slit lenses are shown in FIG. 3 for clarity of illustration, many such structures can be fabricated simultaneously on a single layer. Hundreds of such lenses can be fabricated on a single sheet, and then sawed or micro-machined into parts of the desired size for final assembly. The final assembly, shown in FIG. 4, is a stack of parts, with the vertical chimneys 55 aligned. The illustrative assembly shown in FIG. 4 is about 2"×2" and about 1" thick. It is contemplated that an installation utilizing aerosol particle separators in accordance with this invention would use many such assemblies in air filtration applications. As a front-end for an aerosol measuring device a single stack would usually suffice. They could be mounted for easy removal for periodic cleaning or replacement.

The effectiveness of the aerosol particle separator in accordance with the invention is affected by its proportions and dimensions. As noted above, the dimension of the final orifice or slit is preferably on the order of 25 to 50 microns for optimal removal of the smallest particles within the target particle size range, particularly for respirable particles with diameters ranging from 0.3 to 10 microns. The following analysis was used to develop these dimension ranges and proportions and is offered to assist those skilled in the art in applications for the invention disclosed and claimed herein. However, this analysis is not intended to be interpreted to limit the scope of the invention; the claims and their equivalents are intended to be the definition of the invention.

Figure 5:
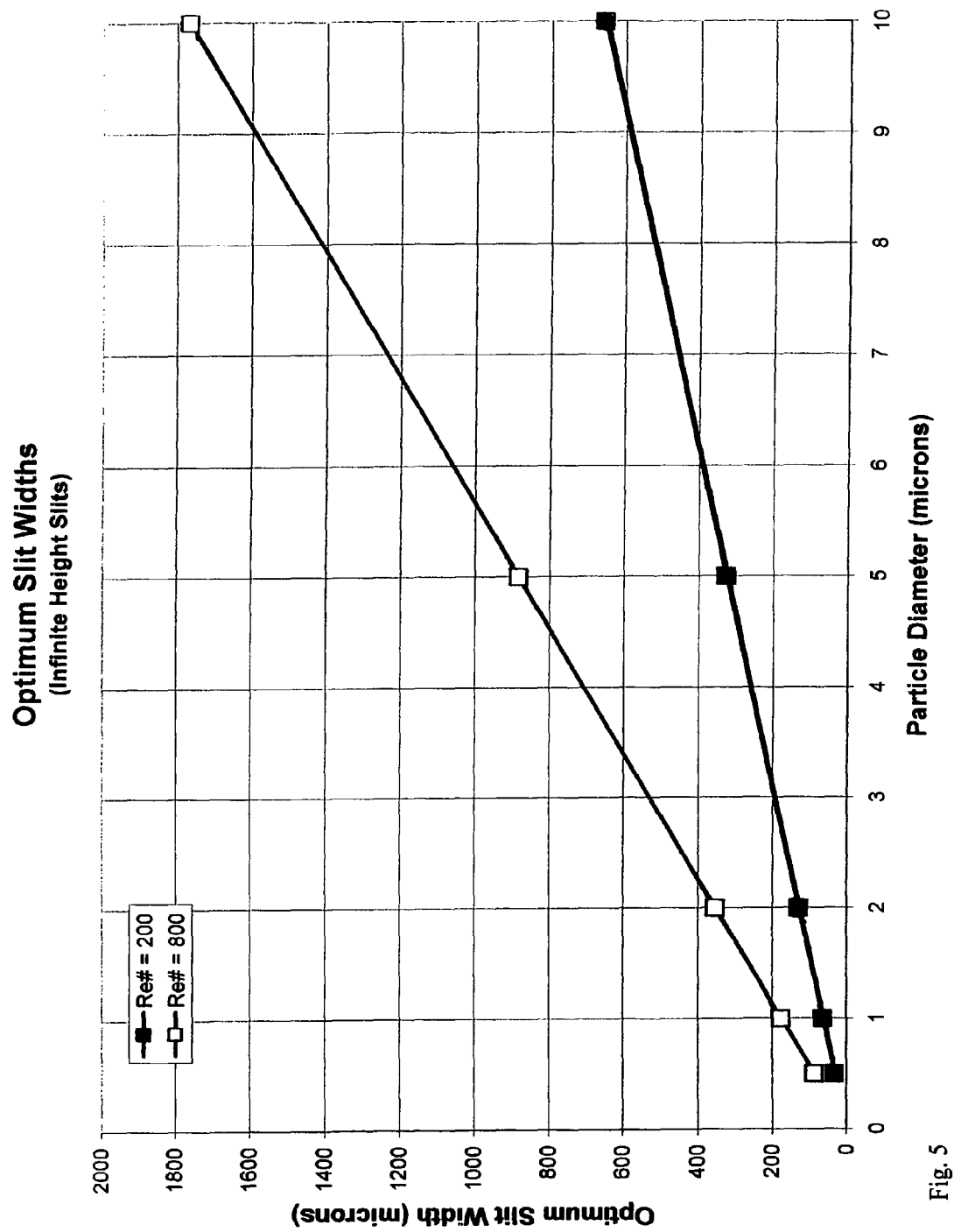
FIG. 5 is a graph illustrating the linear relationship between optimum slit widths and particle diameter for two different Reynolds numbers.

In an aerodynamic slit lens in which the height of the slits is much greater than their widths, the Reynolds number of the flow is constant throughout the lens. Also, the beam contraction factor is the ratio of the distance of a particle from the centerline downstream of the slit (at the point of maximum focusing) to the initial distance from the centerline of the particle upstream of the slit. It has been shown experimentally and through CFD modeling, that the beam contraction factor is linearly proportional to the logarithm of the Stokes number for a given Reynolds number and there is a Stokes number for which the beam contraction factor equals zero implying perfect focusing. Negative contraction factors imply that the aerosol particles cross the centerline and diverge downstream of the focusing lens. These relationships imply that there is an optimum Stokes number which produces nearly perfect focusing for a given particle size, slit width and Reynolds number. Therefore, a unique relationship exists between particle size and optimum slit width for a given Reynolds number. The Stokes number is equal to one $18^{th}$ of the Reynolds number of the flow times the ratio of particle density to air density times the ratio of particle diameter squared to slit width squared. It also represents the ratio of the stopping distance of the particle to the characteristic length of the structure (slit width). The stopping distance is the distance the particle will travel if projected into still air at some initial velocity. The Reynolds number is the ratio of fluid inertial force to the viscous drag force. Since there is an optimum Stokes number for each Reynolds number, the definition of the Stokes number provided above can be rearranged to show that the optimum slit width is directly proportional to the particle diameter. The factor of proportionality is equal to the square root of one $18^{th}$ of the ratio of the Reynolds number to the optimum Stokes number times the ratio of particle density to air density. A plot of this linear relationship is shown in FIG. 5 for two different Reynolds numbers.

Figure 6:
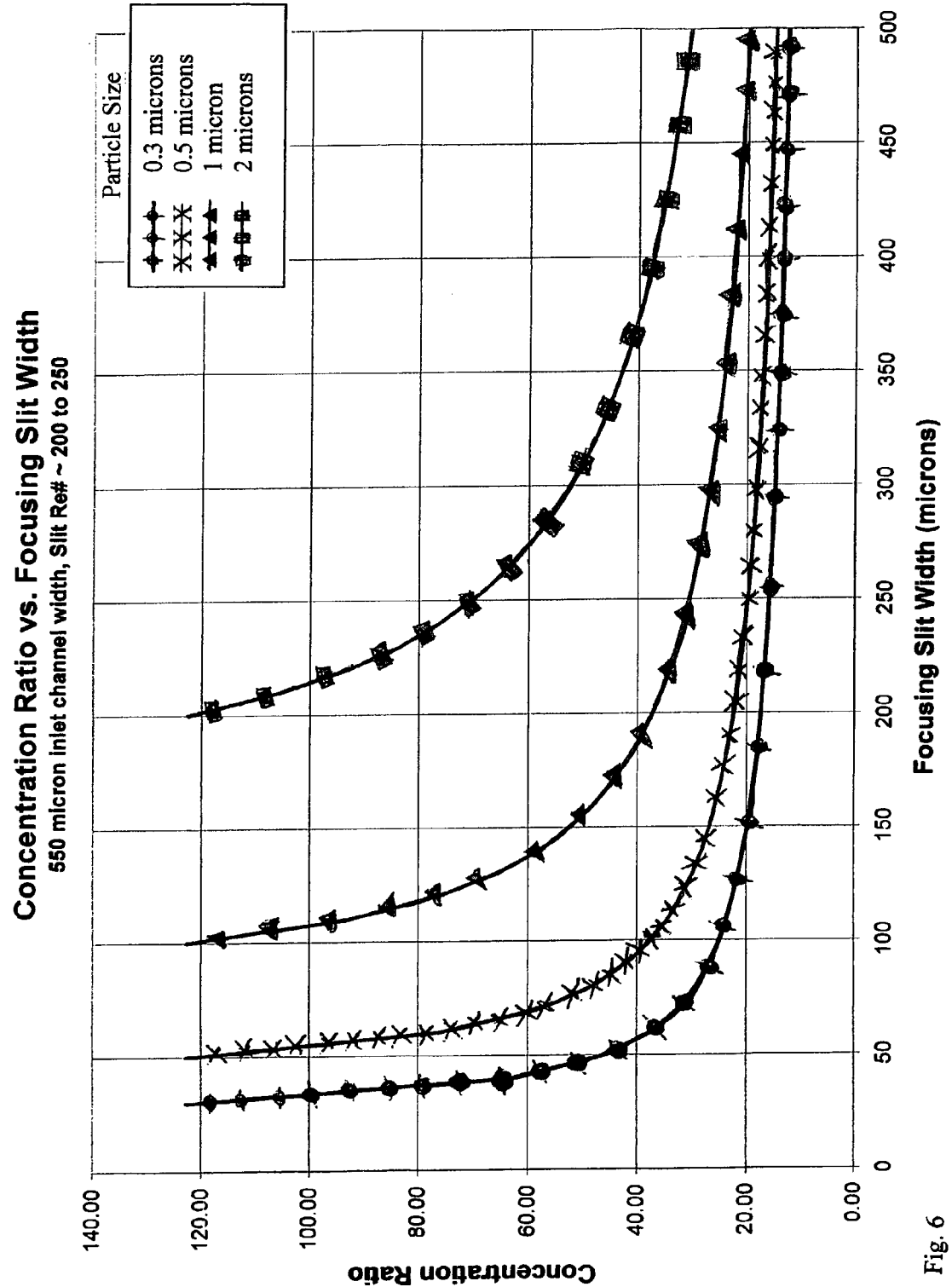
FIGS. 6 and 7 are graphs showing the concentration ratio for several different particle sizes over a range of focusing slit widths.
Figure 7:
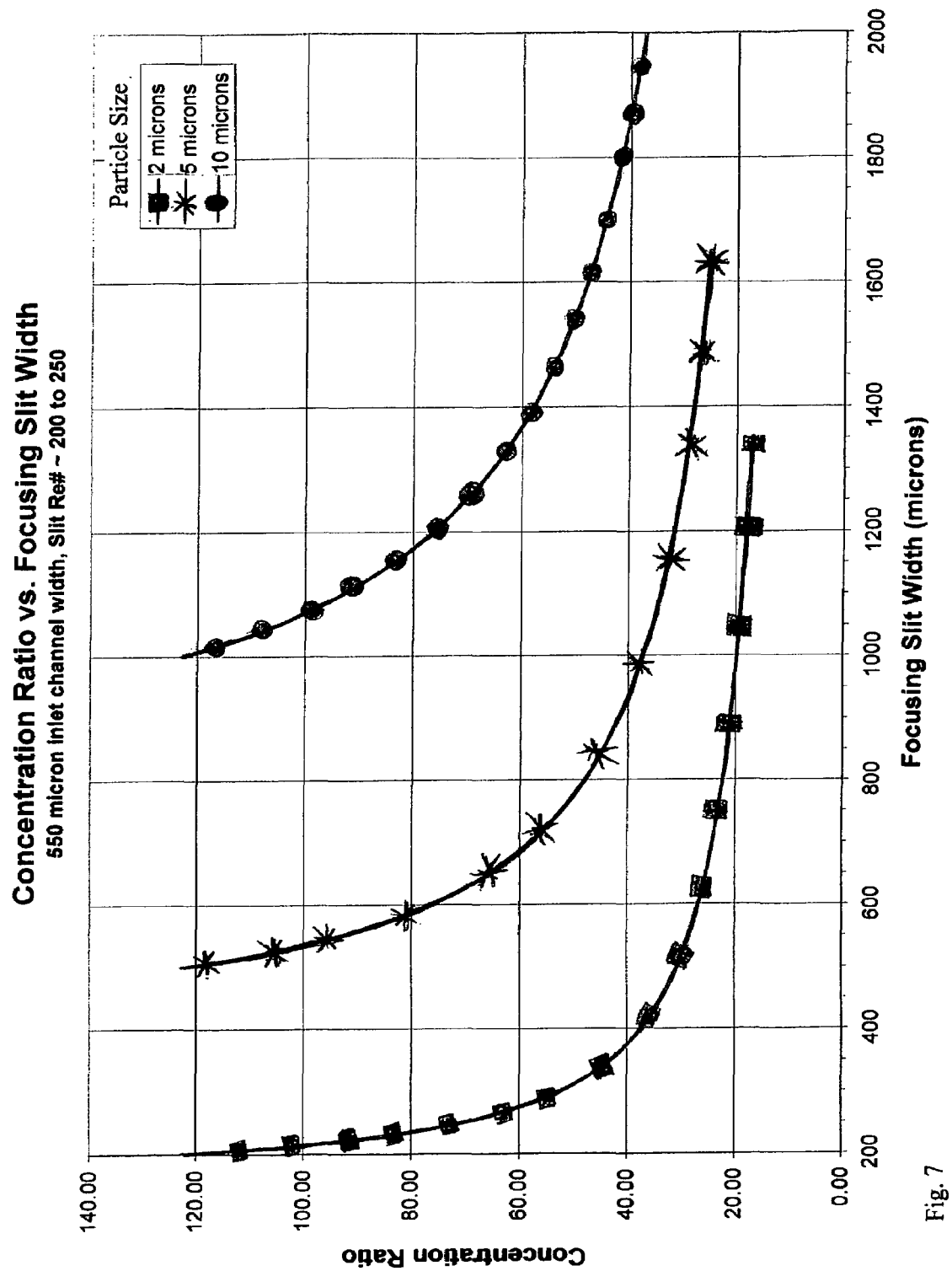

Assuming that the exit slit is wide enough to capture all of the particles in the focused sheet, the concentration ratio will be equal to the ratio of the mass flow of gas entering the aerodynamic lens to the mass flow of gas passing through the exit channel. In the following approximate analysis, the exit slit width 47, 48 is assumed to be 1.5 times as wide as the minimum beam width predicted by the linear relationship between beam contraction factor and the logarithm of the Stokes number. Also, the ratio of the flow rates through the collection slit and the skimmer outlets is assumed to be equal to the ratio of their areas. This assumption is very approximate. Nevertheless, it provides a simple and useful way to estimate the behavior of an aerodynamic lens aerosol concentrator employing a skimmer section and chimneys. The charts in FIGS. 5 and 6 show the relationships between particle size, focusing slit width and concentration ratio predicted by this rough model. The conclusion is that for a given inlet channel width and fluid Reynolds number, the concentration ratio increases with increasing particle size for a fixed focusing slit width. Conversely, the focusing slit width required to focus particles sufficiently to achieve a given concentration ratio increases with increasing particle size. This is illustrated in the graphs in FIGS. 6 and 7.

These model predictions are based upon an aerodynamic lens in which the slit widths through the baffles are assumed to be equal to ⅓ the inlet channel width. Thus, for the 550 micron inlet channel width considered in these examples, the slit width is about 183 microns.

Figure 8:
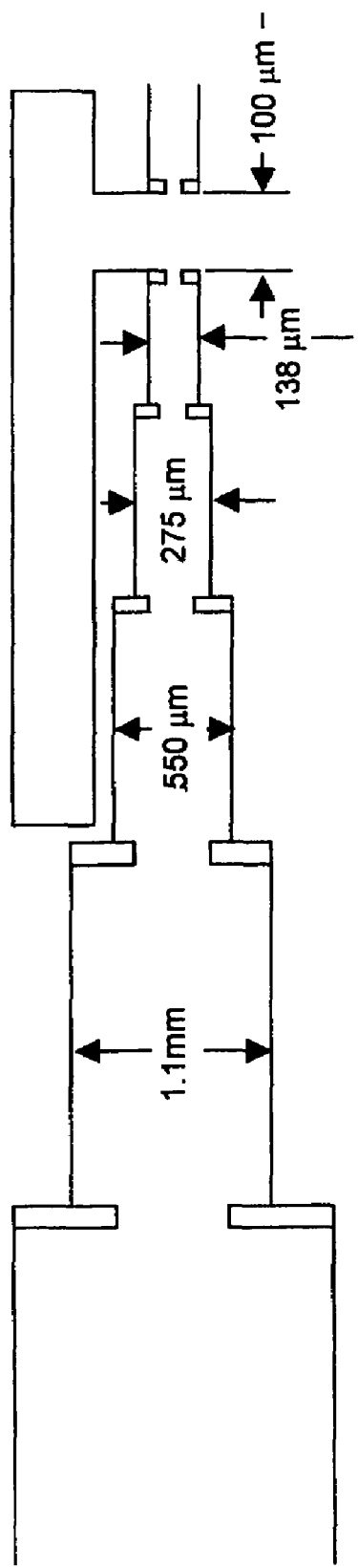
FIG. 8 is a schematic diagram of a representative five-slit aerodynamic lens for particles ranging from 0.5 to 10 microns in diameter.

In a multiple slit lens, the first and largest slit will be sized to provide optimal focusing for the largest particles. Each subsequent slit is sized to provide optimal focusing for the next smaller particle size range. Once the particles of a given size are focused, they should pass through subsequent slits and remain focused (or possibly undergo some additional focusing). In FIG. 8, a representative design for a five-slit lens capable of achieving optimal focusing of 10, 5, 2, 1, and 0.5 micron particles is shown. The slit widths shown on the schematic in FIG. 8 have been selected using the linear relationship between optimum slit width and particle size for a given Reynolds number as described above, as illustrated in the graphs in FIGS. 6 and 7.

A simple spreadsheet model based on the above relationships has been derived to give optimal width dimensions of slits in the several stages of the aerodynamic lens train for optimal focusing of particles in the five size categories noted above. The equations used to generate this model are as follows:

As noted previously, the Stokes # is defined as $$St\# = \frac{\rho_p D_p^2}{18 \rho_{air} \nu_{air} W_{slit}}$$

where
$\rho_p$=particle density
$D_p$=particle diameter
$\rho_{air}$=air density
$\nu_{air}$=air kinematic viscosity
and, $W_{slit}$=slit width This can be expressed as $$St\# = \frac{\rho_p D_p^2}{18 \rho_{air} W_{slit}^2} Re\#$$

The optimum Stokes # is 1.0 for Re#=200 and is 0.55 for Re#=800

The optimum Stokes # is the Stokes number that produces a contraction ratio of zero (perfect focusing).

Assuming there is an optimum Stokes number for any Reynolds number, we can write $$St\#^* = \frac{\rho_p D_p^2}{18\rho_{air} W_{slit}^2} Re\#$$

Or $$W_{slit}^* = \sqrt{\left(\frac{Re\#}{St\#}\right)^* \frac{\rho_p}{18\rho_{air}}} D_p$$

Where the stars represent optimum conditions.

So, for a given optimum Stokes number and Reynolds number combination, the optimum slit width for a given particle size can be calculated with the equation above.

Micro-fabrication Techniques and Assembly Processes

One micro-fabrication technique is the use of Deep Reactive Ion Etching (DRIE) using the patented Bosch Process to etch the flow channels, baffles and other structures entirely through a silicon wafer of a suitable thickness, for example about 1 mm, which has been polished on both sides, and bonded on its bottom surface to a Pyrex glass sheet in which openings for the exhaust flow have been machined or etched. This plasma etching process is capable of forming vertical walls in silicon, usually within one degree of vertical, using a photoresist layer previously patterned on the wafer as an etch mask. DRIE can be used to produce tall structures with walls that are nearly vertical and of uniform thickness—characteristics that are very desirable in the proposed application.

A suitable DRIE process for use with this invention employs an Alcatel 601 DRIE machine and a pulsed gas process in accordance with U.S. Pat. No. 6,127,273 to Laermer et al.

Once the silicon is etched to form the walls of the channels and slit lenses, the flow passage may be closed by bonding onto the top surface either another glass sheet or an identical glass and silicon structure in order to form a second layer and provide a cap for the first layer.

An actual array, fabricated on a 25 mm wide chip, can accommodate roughly 30 parallel channels. The arrays, a portion of which are shown in FIG. 3, can be stacked into a block 40, as shown in FIG. 4, to multiply the flow rate that can be handled by the device. Assembly of the block 40 includes fabricating the required number of arrays shown in FIG. 3 and bonding them together in a stack, with the Pyrex glass sheet of an one array forming the cover for the next adjacent array in the stack. All the layers are precisely positioned with the chimney openings aligned so the particle-free gas 35 can be flow freely out of the block. The glass support layer 15 on the bottom of one array serves as the top cover of the array beneath it creating a compact and structurally robust device. The chimneys in all the layers are aligned, allowing the particle-free exhaust flow 35 to be extracted from the structure at the top and bottom faces of the block.

An example of an assembled block 40, shown in FIG. 4, includes sixteen layers of lens arrays, each containing thirty lens channels, and providing a total of four hundred eighty aerodynamic lenses in a one inch square by 5 mm thick device. Chimneys 20 are provided for the particle-free bulk flow 35 from the skimmers 25, which are an integral part of the lens channels, as previously shown in FIG. 3. Concentrated aerosol sheets 45 exit from the back of the block 40 in low velocity streams. In this example, the device, containing four hundred eighty aerodynamic lens concentrators, each passing about 0.28 liters per minute of flow and achieving a 100:1 concentration factor, can accommodate an inlet flow of about 117 liters per minute.

The aerosol sheets 45 which exit the aerodynamic lens array can all be collected and combined in a small accumulator, accelerated through a converging nozzle, and delivered to another, final aerodynamic lens array which can provide an additional concentration step. This final lens will only have to accommodate $1/100^{th}$ of the inlet flow of the four hundred eighty lenses, roughly 5 times as much as any of the individual lenses in the array. Therefore, this final lens array may consist of only 5 parallel aerodynamic lenses. This two-stage process would provide an overall system concentration factor of at least 3000:1, far greater than can be accomplished with any competing technology. The highly parallel structure envisioned here has an added advantage relative to the long-term performance and robustness of the device. The flow inside the aerodynamic lens structures will be a steady state process, and because of the very small dimensions of the structures, the flow will be laminar (Reynolds numbers <1000). Because of the small particle sizes and the low concentrations, the particles will have no significant impact on the fluid flow fields. Although the small dimensions of the individual passages may result in some pluggage over time, it is anticipated that pluggage of a few passages will not seriously impact the overall performance of the device. As more and more passages become plugged, the pressure drop at a given flow rate will increase. This pressure drop can be monitored and a threshold established for cleaning or replacement of the device. Cleaning can be accomplished by ultrasonically vibrating the structure to fluidize the accumulated particles and back-flushing with pressurized gas to remove the mobilized particles. However, it should be possible to manufacture these devices at low enough cost that periodic replacement will be the preferred approach.

The cost of creating the sixteen chips needed for the device described in FIG. 4 should be low compared with existing technologies, and it is anticipated that in production quantities, this cost would be at least an order of magnitude smaller. Furthermore, once the designs for these devices have been optimized in terms of dimensions and input pressures for particular particle ranges, it will be possible to mass produce them using plastic injection molding or hot embossing processes by selecting materials and processes that provide suitable dimensional stability and hardness. Several companies, such as Wiedmann Plastics Technology, AG, use advanced injection molding techniques to produce plastic parts with feature sizes as small as 5 nm. While the cost of tooling for these methods is high, once the tooling is fabricated, parts can be mass-produced at extremely low cost. Using this approach, the production cost of the aerodynamic lens assembly can be reduced to less than $10.

There are likely some circumstances in which the slit lenses become plugged because of particle size, flow rate, and slit dimensions. Therefore, it may be desirable in some applications to employ a larger scale aerosol separator upstream to remove larger particles, or to employ some other conventional pre-filtering technique to eliminate particles larger than 10 microns.

Silicon micro-machining techniques are routinely used to fabricate structures in the desired size range with extreme precision and repeatability. Although never before attempted in this application, precise alignment of the entire structure using wafer processing methods should be possible. Furthermore, a simple extension of this approach can produce arrays of slit lenses on a silicon chip once the processing steps have been specified and the necessary masks have been produced.

One possible silicon micromachining process that could be used for this purpose is Deep Reactive Ion Etching (DRIE). This process has been shown to be capable of fabricating structures with nearly vertical walls up to a few hundred microns tall. However, an aerodynamic lens employing a slit lens structure would preferably be between 1 and 5 millimeters tall. If a slit lens structure of this scale is beyond the capabilities of the DRIE process, are several other candidate micro-fabrication techniques that are available of this purpose. For example, various rapid prototyping methods have been developed in the last 15 years and have found widespread use in fabricating parts with intricate shapes—primarily in the jewelry industry. These methods have not have been considered capable of affording sufficiently fine resolution to be useful for fabricating very small scale structures with feature dimensions as small as 25 microns, but there are, in fact, several methods that are now beginning to reach the required resolution. Several processes that are used in rapid prototyping: laser-scanned stereo micro-lithography (SLA), image projection SLA, thermojet printing, and various combined techniques are actually capable of producing structures on the desired scale.

In the basic laser-scanned SLA process, a platform mounted on a precision vertical (Z-direction) motorized stage is slowly lowered into a bath of liquid monomer while an ultraviolet laser beam is scanned across the surface of the monomer bath in a computer-controlled pattern generated from a 3-D CAD drawing of the desired part. The UV laser beam photo-polymerizes the monomer to produce a solid polymer in a pattern dictated by the path of the scanning laser beam. The part is generated layer by layer and can be up to several tens of centimeters tall. Most such machines have lateral resolution on the order of 100 microns or greater, so they are not likely candidates for fabricating aerodynamic lenses suitable for focusing submicron particles at atmospheric pressure.

Image projection SLA machines utilize an ultraviolet lamp to produce a wide area beam which is focused onto the monomer surface using a micro-mirror array spatial light modulator. This micro-mirror array can be computer controlled to produce a very high resolution image of a slice of the desired part. One such machine, produced by EnvisionTec, can produce parts with minimum feature sizes in the 25 micron range and produces layers with approximately 16 micron thickness. This process may be very well suited to the fabrication of aerodynamic slit lenses.

Several companies offer thermojet printing machines that utilize ink-jet technology to fire small droplets of molten thermoplastic or wax in a computer-controlled pattern to build up a part in layers as with the SLA process except that the thermojet process does not require a bath of monomer. In one variation of this process, an ink-jet printing head is used to fire droplets of liquid monomer onto the structure being fabricated and a synchronized UV flash lamp is used to polymerize the monomer as it impacts the part. This machine—manufactured by Stratasys—can achieve a resolution of about 40 to 80 microns in the horizontal plane.

With any of these processes, the parts produced are either wax or plastic. The wax materials are too fragile to be used in an aerodynamic lens structure, but some of the plastics—such as polycarbonate or ABS—may be suitable. If added abrasion resistance is required, these plastic parts can be coated with a very thin vacuum-deposited metal layer. Alternatively, these plastic parts could be used to form a metal mold using a plating process and the metal mold could then be used in an injection molding or hot embossing process to mass-produce the aerodynamic lens structures.

Another possible process for micro-fabricating the aerodynamic lens structures is a process called X-ray LIGA. In this process, a tightly focused high intensity x-ray beam derived from a synchrotron is projected onto a plastic block. mounted on an X-Y translation stage. Where the block is exposed to the x-rays, the bonds in the plastic polymer are broken and the plastic can be etched away. The x-ray beam is extremely well collimated, so it can etch features that are many millimeters deep, and because the beam can be tightly focused, this process can produce features down to about 1 micron in size. The resulting part can then be electroplated to produce a solid nickel negative of the etched plastic part and that nickel piece can be used as a hot-embossing stamp or for injection molding. The cost of producing the original piece by this process is quite high, but a hot embossing stamp can be used to stamp out many hundreds of thousands of parts at very low per piece cost. This process may be attractive for commercial production of aerodynamic lens arrays.

The preferred embodiment of the invention presented here takes advantage of highly developed micro-fabrication techniques and applies them to the manufacture of a new aerodynamic slit lens array concentrator. By taking advantage of the high degree of parallelism that can easily be achieved with silicon wafer processing methods or with various other micro-fabricating methods, a new generation aerosol concentrator capable of extremely high concentration factors and reasonably high throughput can be produced. The device is extremely compact and lightweight, and it is possible to mass produce these devices at relatively low unit cost. Another benefit of the aerodynamic aerosol particle separators disclosed herein is that they are expected to be much more energy efficient than any existing technology. Preliminary estimates of the performance of an aerodynamic slit lens array show that the pressure drop through such an array would be roughly an order of magnitude less than that of a conventional HEPA filter handling the same air flow rate.

The low cost, compact nature, simplicity, and effectiveness of these make them ideally applicable for many applications, including the use as the front end of biological agent detectors, such as Bioagent Autonomous Networked Detectors (BAND)—"detect-to-treat" system and Rapid Automated Biological Identification System (RABIS)—"detect-to-protect" system detectors, and for environmental monitoring systems including ambient air quality monitoring and industrial monitoring.

Lens array chips, and stacks of lens array chips may be fabricated for large scale particle removal and gas cleaning applications. Combining the outputs of arrays of aerodynamic lens concentrators and performing a second stage concentration with one or more additional aerodynamic lenses should offer economical and effective particle removal from large volume flow streams in many applications, including use as a replacement for High Efficiency Particulate Air (HEPA) and other filters (e.g., for diesel particles). A complete aerosol concentrator device will include plumbing and flow control components in addition to the aerodynamic lens array. I anticipate that the aerodynamic lens array will be a disposable component of the system whereas the pumps, flow meters and flow controllers will be long-life components.

Obviously, numerous modifications and variations of the described preferred embodiment are possible and will occur to those skilled in the art in light of this disclosure of the invention. Accordingly, I intend that these modifications and variations, and the equivalents thereof, be included within the spirit and scope of the invention as defined in the following claims, wherein

I claim:

1. A device for concentrating aerosols in a gas stream and removing said aerosols from said gas stream, comprising:
   an aerodynamic lens array including a multiplicity of aerodynamic lenses, each having an input end and an output end, and an internal flow channel extending between said input end and said output end, with a series of internal slit orifices through baffles extending laterally into said internal flow channel, and a final slit orifice through which a concentrated aerosol sheet emerges from said output end, said slit orifices decreasing in width from said input end to said output end;
   said baffles including walls that project into said internal flow channel presenting a surface facing said input end, and an opposite surface facing said output end;
   each aerodynamic lens includes a skimmer opening upstream of said output end for particle-free bulk gas flow through said skimmer openings to an integral chimney;
   said aerodynamic lens has substantially vertical walls and substantially vertical surfaces defining said slit orifices;
   said aerodynamic lens array having multiple layers of aerodynamic lenses, each layer having multiple aerodynamic lenses in a parallel, side-by-side rank, and banks of lenses in a stack of said parallel ranks to multiply the available flow rate through the device.

2. A device as defined in claim 1, wherein:
   said multiple aerodynamic lenses in said parallel, side-by-side rank are in a single unitary structure made using micro-fabrication techniques.

3. A device as defined in claim 2, wherein:
   said layers of side-by-side ranks of said lenses are stacked with said chimneys aligned to provide for combined particle-free bulk gas flow from aligned aerodynamic lenses in each layer.

4. A device as defined in claim 1, wherein:
   said lens array is fabricated in plastic using hot embossing or injection molding techniques.

5. A device as defined in claim 1, wherein:
   said final slit width dimension is on the order of 25 to 50 microns.

6. A device as defined in claim 4, wherein:
   said aerosols have particle diameters predominately in the range of about 0.05 to 10 microns.

7. A device as defined in claim 6, wherein:
   said slit widths have a range decreasing from an inlet slit of about 1000 microns wide to an exit slit of less than about 50 microns wide.

8. A device as defined in claim 1, further comprising:
   a skimmer at the exit of each lens in the assembly, including a connecting channel to chimneys linking the skimmers of lenses in vertical alignment in the stack;
   whereby the bulk of the gas flow is stripped off while allowing the concentrated particle stream to pass into a region of much lower flow rate, thereby producing a highly concentrated aerosol in the low velocity stream.

9. A process for making an aerodynamic lens array for concentration and removal of particles in an aerosol, comprising:
   fabricating a unitary micro-structure defining side walls of a plurality of parallel aerodynamic lenses having a pattern of said aerodynamic lenses, each aerodynamic lens pattern having an input end and an output end, and an internal flow channel extending between said input end and said output end, with a series of internal slit orifices through baffles projecting laterally into said internal flow channel, said baffles including walls that project into said internal flow channel presenting a surface facing said input end, and an opposite surface facing said output end, and a final slit orifice at said output end, and a skimmer opening in said flow channel immediately upstream of said final slit orifice and communicating with one or more chimneys in the vicinity of said output end of said flow channel for egress of substantially particle-free gas;
   stacking a multiplicity of said aerodynamic lens arrays together in a bank of layers, with said chimneys aligned to afford a series of continuous chimneys through which said particle-free gas exits said block.

10. A process for concentrating aerosols in a gas stream to a narrow beam or sheet of particles for removal from said gas stream and analysis for environmental monitoring, comprising:
    conveying a dilute aerosol-laden gas stream into an input end of an aerodynamic lens array, said array including a multiplicity of micro-fabricated aerodynamic lenses, each having an input end and an output end, and an internal flow channel in each lens along a centerline extending between said input end and said output end, with a series of internal slit orifices through baffles in said internal flow channel, said baffles including walls that project into said internal flow channel presenting a surface facing said input end, and an opposite surface facing said output end, and a final slit orifice at said output end;
    migrating said aerosol particles toward said centerline in each flow channel as said aerosol-laden gas stream proceeds through said flow channel to concentrate said particles toward said centerline;
    skimming off gas that is substantially free of aerosol particles through chimneys connected to skimmers communicating with said flow channel adjacent to each of said output ends;
    collecting concentrated particle streams in a much lower flow velocity stream for monitoring of environmental quality.

11. A process for removing aerosols from air to produce clean air, comprising:
    conveying a dilute aerosol-laden gas stream into a aerodynamic lens array, said array including a multiplicity of micro-fabricated aerodynamic lenses, each having an input end and an output end, and an internal flow channel in each lens along a centerline extending between said input end and said output end, with a series of internal slit orifices through baffles in said internal flow channel, said baffles including walls that project into said internal flow channel presenting a surface facing said input end, and an opposite surface facing said output end, and a final slit orifice at said output end;

migrating said aerosol particles toward said centerline in each flow channel as said aerosol-laden gas stream proceeds through said flow channel to concentrate said particles toward said centerline; and skimming off air that is substantially free of aerosol particles through chimneys connected to skimmers communicating with said flow channel adjacent to each of said output ends;

collecting aerosol particles from concentrated particle streams at said output end in a region of much lower flow rate for disposal.

12. A process as defined in claim 11, wherein:

said collecting is in a collection chamber having a restricted opening at a collection channel inlet communicating with said skimmers, said restricted opening including a slit through a front wall across said collection channel and presenting a surface facing said output end and bounding an area of significantly larger width downstream of said collection channel inlet.

\* \* \* \* \*